United States Patent [19]

Gueant et al.

[11] 4,049,725

[45] Sept. 20, 1977

[54] METHOD FOR PREPARING PRIMARY ALCOHOLS HAVING ALKYLS BRANCHED AT THE SECOND CARBON

[75] Inventors: Auguste Gueant, Lens; Serge Mercier, Paris, both of France

[73] Assignee: Produits Chimiques Ugine Kuhlmann, Paris, France

[21] Appl. No.: 570,829

[22] Filed: Apr. 23, 1975

[30] Foreign Application Priority Data

Apr. 30, 1974 France .................. 74.14962

[51] Int. Cl.² .................. C07C 29/14; C07C 45/08
[52] U.S. Cl. .................. 260/638 B; 260/604 HF
[58] Field of Search .................. 260/638 B, 604 HF

[56] References Cited

U.S. PATENT DOCUMENTS

| 2,137,407 | 11/1938 | Lazier | 260/638 B |
|---|---|---|---|
| 2,322,098 | 6/1943 | Schmidt | 260/638 B |
| 2,614,107 | 10/1952 | Wender et al. | 260/638 B |
| 2,670,378 | 2/1954 | Frye | 260/638 B |
| 2,694,091 | 11/1954 | Harvey et al. | 260/638 B |
| 2,695,315 | 11/1954 | Parker | 260/638 HF |
| 3,102,150 | 8/1963 | Hunter et al. | 260/638 B |
| 3,341,610 | 9/1967 | Dunlop et al. | 260/638 B |
| 3,647,842 | 3/1972 | Wilkes | 260/638 B |
| 3,925,490 | 12/1975 | Reich et al. | 260/638 B |

OTHER PUBLICATIONS

Hatch, "Higher Oxo Alcohols", 1957, pp. 2-6, 22, 23.

*Primary Examiner*—Joseph E. Evans
*Attorney, Agent, or Firm*—Pennie & Edmonds

[57] ABSTRACT

Aldehydes branched at the second carbon are surprisingly hydrogenated selectively in good yield to the corresponding primary alcohols over a copper catalyst by using a hydrogen/carbon monoxide mixture having molar ratio about 2/1; simultaneously said mixture is depleted of hydrogen to a level where it can be used directly in the Oxo-hydroformylation process without further pretreatment.

10 Claims, No Drawings

METHOD FOR PREPARING PRIMARY ALCOHOLS HAVING ALKYLS BRANCHED AT THE SECOND CARBON

The present invention provides a procedure for preparing in high yield primary alcohols whose alkyls are branched at the second carbon atom, by hydrogenating the corresponding aldehydes in liquid phase.

BACKGROUND OF THE INVENTION

It is known that aldehydes can be prepared according to the general scheme (1) by the Oxo-synthesis which comprises hydroformylating olefins or olefinic compounds with carbon monoxide and hydrogen in the presence of a cobalt catalyst:

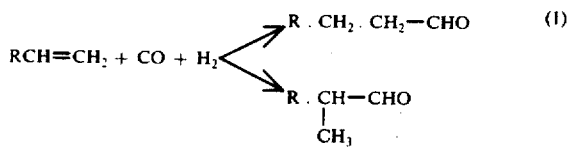

It is also known to prepare aldehydes branched at the second or alpha carbon by aldolization in alkaline medium, followed by dehydration or crotonization according to scheme (2), starting with two straight-chained aldehyde molecules, a straight-chained plus a branched aldehyde, or two branched aldehydes with the condition that at least one of the two reacting aldehydes is not branched at the alpha carbon. All these starting aldehydes can be obtained by Oxo-synthesis.

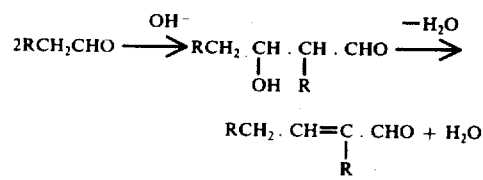

The branched aldehydes formed according the scheme (2) can be transformed by hydrogenation in liquid phase according to scheme (3).

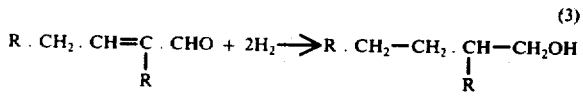

In the schematic equations (1), (2) and (3) the R's represent any straight or branched alkyl group.

Hydroformylation of olefinic hydrocarbons according to scheme (1) is exemplarily effected in the presence of cobalt carbonyl catalyst under pressures from about 100 to 300 bars and at temperatures in the range of from about 100° to 200° C using a mixture of hydrogen and carbon monoxide with molar ratio $H_2/CO$ in the range of from about 1.1/1 to 1.5/1, usually obtained by gaseous cracking of methane. The Oxo reaction requires a well-controlled ratio of $H_2/CO$ in order to ensure stability of the cobalt carbonyl which necessitates a partial pressure of CO sufficient to prevent its decomposition.

The preparation of the necessary gaseous mixture of hydrogen and carbon monoxide therefore requires a special gas-cracking treatment which comprises first separating the components from each other either by physical means at low temperatures around −50° C or by chemical means. The separated carbon monoxide and hydrogen are then combined in a ratio suitable for the Oxo process and the excess hydrogen can serve to hydrogenate the aldehydes to alcohols. The preliminary treatment necessitates accessory installations which are complex and burdensome.

SUMMARY OF THE INVENTION

Present inventors have discovered surprisingly that aldehydes branched at the second carbon are hydrogenated selectively to the corresponding primary alcohols by a hydrogen/carbon monoxide mixture having a molar composition in the neighborhood of 2/1. This is unexpected in view of the fact that such selectivity is not found when straight-chained aldehydes are used, or when the aldehyde is branched at a position other than the second carbon. In such cases the common result is to produce considerable quantities of high-boiling substances resulting from dimerization and the like.

This discovery now makes it possible to prepare primary alcohols having alkyl branched at the second carbon, by direct hydrogenation of the corresponding aldehydes using a gas such as is available by oxidative cracking of methanes. As long as this gas has a composition in the range of about 2/1 mols of hydrogen per mol of carbon monoxide (about 1.6/1 to 2.2/.1 being advantageous), the gas does not have to be submitted to a special preliminary treatment. Furthermore by using the gas in amounts such as to change its molar ratio $H_2/CO$ to between about 1/1 and 1.5/1, the exiting gas can subsequently be used in the Oxo-synthesis process, exemplarily in the preparation of the aldehydes to be hydrogenated, using steps such as discussed above.

Briefly stated, the present invention is a method for preparing a primary alcohol branched at the second carbon which method comprises reacting a corresponding saturated or unsaturated aldehyde with a hydrogen/carbon monoxide gas mixture containing about 2 mols of hydrogen per mol of carbon monoxide over a hydrogenating catalyst which will not form metal carbonyls, and continuing the reaction until the molar ratio hydrogen/carbon monoxide in the gas mixture reaches between about 1/1 and 1.5/1.

The invention also provides for using the exit gases, enriched in carbon monoxide, as the hydroformylating agent in the Oxo process.

DETAILED DESCRIPTION

The preferred gas mixture to be used in carrying out the method of this invention is a synthetic gas formed by cracking methane and having a molar ratio $H_2/CO$ between about 1.6/1 and 2.2/1, most preferably between about 1.8/1 and 2/1. This is used without further preliminary treatment to hydrogenate an aldehyde having a branch at the alpha carbon. The residual gas is hydrogendepleted to leave a composition between about 1.1/1 and 1.5/1 which is suitable for use in the Oxo process, thereby eliminating the expensive and burdensome steps used in the prior art to prepare hydroformylation agent specially. In particular the effluent gas mixture can be used directly for preparing aldehydes, which can subsequently be submitted to the above described steps of aldolization and crotonization to aldehydes having alkyl branching at the second carbon and useful in the present hydrogenation step.

The hydrogenation catalysts useful for the present hydrogenation by a $H_2/CO$ mixture are in particular those based on copper which are specially appropriate because they are insensitive to carbon monoxide. However any hydrogenation catalyst which is insensitive to carbon monoxide can likewise be used. When copper is used, it can contain as primers, promoters or the like, one or more other metals or metal oxides, with the exception of group VIII elements in the periodic chart; thus cobalt and nickel are contraindicated because they would cause deterioration of catalyst by forming metal carbonyls which would dissolve in the reaction products.

Among the catalysts, Adkins catalysts based on copper and chromic oxide $Cr_2O_3$ are specially suitable, particularly when stabilized by stabilizers such as barium oxide. These catalysts can be prepared in various known ways. In a particularly convenient procedure, an aqueous alkali is added to an aqueous solution of the nitrates of the respective metals. The precipitated hydroxide or hydrated oxide is successively washed, dried, calcined and formed into pellets. The catalysts are then activated before being placed into use by treatment with hydrogen or carbon monoxide at a temperature between about 130° and 240° C.

The relative quantities of the different components entering the composition of the catalyst can be varied over a wide range of proportions. Present inventors have found in particular that catalysts of $Cu/Cr_2O_3/BaO$ comprising about 30–40% by weight of copper, about 50–60% $Cr_2O_3$ and about 5–15% BaO are particularly suitable for preparation for example of 2-ethylhexanol by hydrogenation in liquid phase to 2-ethylhexenal.

With such catalysts the hydrogenation takes place in satisfactory manner in the liquid phase at temperatures between about 100° and 250° C and at pressures higher than about 10 bars, the best results being obtained with temperatures between about 150° and 180° C under pressures between 50 and 100 bars.

While any aldehyde can be submitted to hydrogenation by an approximately 2/1 molar mixture of hydrogen and carbon monoxide, those having the high selectivity characteristic of the present invention are the saturated and unsaturated aldehydes which are branched at the second or alpha carbon atom. Thus, n-butyric aldehyde produces a less than 90% yield of butanol, the remainder going in side reactions to high-boiling products; whereas isobutyric aldehyde produces an almost quantitative yield of isobutanol. When the aldehyde has unsaturation, the hydrogenated product obtained by the method of this invention is the corresponding completely hydrogenated or saturated primary alcohol. Thus, 2-ethyl-2-hexenal, 2-ethyl-3-hexenal, 2-ethyl-4-hexenal and 2-ethyl-5-hexenal all yield 2-ethyl hexanol. Of these, 2-ethyl-2hexenal is obtainable by the successive steps of (i) hydroformylating propylene in the Oxo process to yield n-butanal (ii) submitting this n-butanal to an aldo condensation under alkaline conditions to yield 2-ethyl-3-hydroxy-hexanal and then (iii) dehydrating ("crotonizing") this 2-ethyl-3-hydroxy-hexanal to give the 2-ethyl-2hexenal.

Thus the procedure of this invention is particularly suitable for hydrogenating branched aldehydes prepared first by such successive aldolization and crotonization of Oxo aldehydes, inasmuch as in such an overall process, the synthetic gas is used without preliminary treatment to effect the hydrogenation and then directly used for the Oxo-synthesis.

Any primary alcohols having an alkyl branched at the second carbon can be prepared by this method. The results have been found especially satisfactory in obtaining 2-ethylhexanol from 2-ethyl-2-hexenal (i.e. 2-ethyl-2-hexen-1-al)
isobutanol from 2-methyl-2-propen-al
2-methyl-pentanol from 2-methyl-2-pentenal 2-propyl-heptanol from 2-propyl-2-heptenal
2-propyl-5-methyl-hexanol (i.e. 2-propyl-5-methyl-1-hexanol from 2-propyl-5-methyl-2-hexen-1-al In summary, the aldehydes hydrogenated by the method of this invention include those having the generic formula

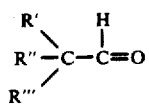

wherein R' is H or alkyl and wherein R'' and R''' and R' when it is alkyl are the same or different $C_1 - C_{20}$ straight or branched, saturated or unsaturated alkyl or where R'' and R''' together may be a methylene or alkyl-substituted methylene having the formula

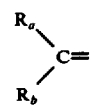

wherein $R_a$ and $R_b$ are the same or different H or $C_1 - C_{20}$ straight or branched, saturated or unsaturated alkyl.

Primary alcohols are known to have many uses varying from uses as solvents, lubricants and defoamers to myriad applications as raw materials for the manufacture of surfactants, drugs and cosmetics. See Kirk-Othmer, ENCYCLOPEDIA OF CHEMICAL TECHNOLOGY, Second Edition, Volume 1, pages 531–569 (1963).

The invention will be further illustrated by description in connection with the following specific examples of the practice of it, wherein proportions are in parts by weight unless stated otherwise.

EXAMPLE 1

A tubular reactor, 2.5 cm in diameter and 2.1 meters high, is thermostated at 160° C by a water jacket and contains a liter of Adkins catalyst having composition by weight equal to 40/50/10 of $Cu/Cr_2O_3/BaO$. A continuous stream of 2-ethyl-2-hexenal is passed through this reactor under 50 bars pressure at a rate of 415 grams per hours. Simultaneously, a mixture of hydrogen and carbon monoxide having molar ratio $H_2/CO$ equal to 2 is introduced at the rate of 500 liters per hour.

The hydrogenated product obtained has the following composition by weight:

| | |
|---|---|
| 2-ethyl-hexanal | 0.02 |
| 2-ethyl-2-hexenol | 0.08 |
| 2-ethylhexanol | 99.1 |
| High boiling substances | 0.8 |

The exiting gas contains hydrogen and carbon monoxide in the molar ratio $H_2/CO = 1.11$ which is utilizable directly for an Oxo-synthesis, as in particular for the hydroformylation of propylene to form n-butanal as the first step in preparation for adolization and crotonization to yield 2-ethyl-2-hexenal.

EXAMPLE 2

This example illustrates that poor yields are obtained when it is attempted to convert a straight chain aldehyde to the corresponding alcohol with a $H_2/CO$ mixture, i.e. it shows that the reaction of a $H_2/CO$ mixture and a straight-chain aldehyde in the presence of the same catalyst is non-selective.

Following the procedure of Example 1, the reactor is again charged with Adkins catalyst and a continuous stream of n-butanal is applied at 140° C, under 50 bars pressure and at a rate of 430 grams per hour. A parallel stream of carbon monoxide-hydrogen mixture, having a molar ratio $H_2/CO$ equal to 2, is also passed through to effectuate hydrogenation.

The obtained product of hydrogenation has the following composition by weight:

| butyric aldehyde | 0.05 |
|---|---|
| dibutyl oxide | 0.05 |
| butanol | 89.1 |
| high boiling materials | 10.8 | corresponding to about 10 times as much by-product as in the preceding example.

The gas emerging at 316 liters per hour contains hydrogen and carbon monoxide in the molar ratio $H_2/CO=1.12$.

This is not an example of the instant invention which provides a method of preparing in good yield alcohols whose alkyls are branched at the second carbon, starting with the corresponding alpha-branched aldehydes.

EXAMPLE 3

This example is not an illustration of the instant invention but shows in contrast a non-selectivity when all the conditions of the instant invention are used except that the aldehyde treated is branched in a manner other than at the second or alpha carbon.

A reactor as in Example 1 is charged with Adkins catalyst of the same composition but treated with a continuous stream of 426 grams per hour of 3,5,5-trimethyl-hexanal at 140° C under 50 bars pressure. Hydrogenation is effectuated by introducing simultaneously 235 liters per hour of a hydrogen-carbon monoxide mixture having molar ratio $H_2/CO$ equal to 2.

This obtained hydrogenated product has the following composition by weight:

| 3,5,5-trimethyl-2-hexanal | 0.25 |
|---|---|
| 3,5,5-trimethyl hexanol | 94.00 |
| High boiling substances | 5.75. |

This gas emerging at 158 liters per hour contains hydrogen and carbon monoxide in the molar proportion $H_2/CO=1.10$.

EXAMPLE 4

Using the procedure and catalyst as in Example 1, at 140° C and 50 bars pressure, a continuous stream of 430 grams per hour of isobutanal is hydrogenated in the presence of a parallel current of 475 liters/hour of a mixture of hydrogen and carbon monoxide having molar ratio $H_2/CO$ equal to 1.8.

The hydrogenated product has the following composition by weight:

| isobutanal | 0.05 |
|---|---|
| diisobutyl ether | 0.15 |
| isobutanol | 98.8 |
| High boiling substances | 1.2. |

EXAMPLE 5

Using the procedure and catalyst as in Example 1 with temperature at 160° C and pressure at 50 bars, the simultaneous streams are (a) 400 grams per hour of an ethylenically unsaturated $C_{18}$ aldehyde[a] obtained by aldolization and subsequent crotonization of 3,5,5-trimethyl-hexanal and (b) 225 liters of a mixture of hydrogen and carbon monoxide having a molar ratio $H_2/CO=2$.

The obtained hydrogenated product has the following composition by weight:

| $C_{18}$ ethylenic aldehyde[a] | 0.05 |
|---|---|
| $C_{18}$ ethylenic alcohol | 0.15 |
| $C_{18}$ saturated alcohol[b] | 99.2 |
| High boiling substances | 0.6. |

[a] having the formula 5, 7, 7-trimethyl-2-[1', 3', 3'-trimethyl-butyl]-2-octenal,
[b] having the formula 5, 7, 7 trimethyl-2-[1', 3', 3'-trimethyl butyl]-2-octanol.

The gas emerging at 150 liters per hour contains hydrogen and carbon monoxide in the molar ratio $H_2/CO=1.10$.

EXAMPLE 6

A stainless steel autoclave of capacity 2.3 liters is equipped with agitation and heating means. A 100 gram quantity of 2-ethyl-2-hexenal is introduced, also 20 grams of a powdered catalyst having the composition by weight

| Cu | 40 |
|---|---|
| $Cr_2O_3$ | 50 |
| BaO | 10. |

A gaseous mixture of hydrogen and carbon monoxide having molar ratio $H_2/CO=2$ is introduced under 70 bars pressure. The autoclave is then heated to 120° C and the temperature is raised from 120° to 160° C over a period of 3 hours.

The autoclave is then cooled to ambient temperature. The hydrogenated product is separated from catalyst by filtration and found to have the following composition by weight:

| 2-ethyl-hexanal | 0.05 |
|---|---|
| 2-ethyl-2-hexenol | 0.15 |
| 2-ethyl-hexanol | 99.2 |
| High boiling substances | 0.6. |

EXAMPLE 7

The procedure of Example 6 is followed in all details except that the 20 grams of $Cu/Cr_2O_3/BaO$ catalyst is replaced by 20 grams of a copper/zinc oxide catalyst having the composition by weight equal to 40 parts Cu and 60 parts ZnO.

The recovered hydrogenated product has the following composition by weight:

| | |
|---|---|
| 2-ethylhexanal | 0.05 |
| 2-ethyl-2-hexenal | 0.15 |
| 2-ethylhexanol | 98.6 |
| High boiling substances | 1.2. |

We claim:

1. A method for preparing a primary alkyl alcohol branched at the second carbon atom which comprises reacting over a hydrogenation catalyst which is insensitive to carbon monoxide under the reaction conditions and which does not form metal carbonyls a. an aldehyde, in the liquid phase, of formula

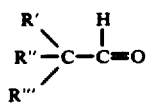

wherein R' is H or alkyl and wherein R" and R''', and R' when it is alkyl, are the same or different $C_1$–$C_{20}$ straight or branched alkyl or alkenyl or wherein R" and R''' together may be a methylene or an alkyl-substituted methylene having the formula

wherein $R_a$ and $R_b$, which can be the same or different, are H or $C_1$–$C_{20}$ straight or branched alkyl or alkenyl, with b. a hydrogen/carbon monoxide gas mixture having a molar ratio of about 2/1, and continuing the reaction until the residual hydrogen/carbon monoxide molar ratio in the gas mixture reaches between about 1/1 and 1.5/1.

2. The method of claim 1 wherein the initial hydrogen/carbon monoxide mixture contains from about 1.6 to 2.2 mols of hydrogen per mol of carbon monoxide.

3. The method of claim 1 wherein the reaction is carried out at a temperature between about 100° and 250° C and at a pressure greater than about 10 bars.

4. The method of claim 3 wherein the reaction is carried about at a temperature between about 150° to 180° C and at a pressure between about 50 to 100 bars.

5. The method of claim 1 wherein the hydrogenation catalyst is based upon copper.

6. The method of claim 5 wherein the hydrogenation catalyst is a copper/chromic oxide Adkins catalyst.

7. The method of claim 6 wherein the hydrogenation catalyst is a $Cu/Cr_2O_3/BaO$ catalyst comprised of about 30–40% by weight copper, about 40–60% by weight chromic oxide, and about 5–15% barium oxide.

8. The method of claim 1 wherein the aldehyde is 2-ethylhexanal or isobutanal.

9. A method comprising reacting over a hydrogenation catalyst which is insensitive to carbon monoxide under the reaction conditions and which does not form metal carbonyls a. an aldehyde, in the liquid phase, of formula

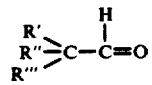

wherein R' is H or alkyl and wherein R" and R''', and R' when it is alkyl, are the same or different $C_1$–$C_{20}$ straight or branched alkyl or alkenyl or wherein R" and R''' together may be a methylene or an alkyl-substituted methylene having the formula

wherein $R_a$ and $R_b$, which can be the same or different, are H or $C_1$–$C_{20}$ straight or branched alkyl or alkenyl, with b. a hydrogen/carbon monoxide gas mixture having a molar ratio of about 2/1, continuing the reaction until the residual hydrogen/carbon monoxide molar ratio in the gas mixture reaches between about 1/1 and 1.5/1 and a primary alkyl alcohol branched at the second carbon atom is formed, separating said residual gas mixture from said reaction, and employing said residual gas mixture as a hydroformylation agent in the Oxo process to form an aldehyde.

10. The method of claim 9 wherein the resulting gas mixture is employed as a hydroformulating agent in an Oxo-synthesis to produce the aldehyde of step (a).

* * * * *